US008839962B2

(12) United States Patent
Brunsvik

(10) Patent No.: US 8,839,962 B2
(45) Date of Patent: Sep. 23, 2014

(54) SEPARATION AND/OR PURIFICATION OF $B_0$ FROM $C_0$

(75) Inventor: Anders Brunsvik, Trondheim (NO)

(73) Assignee: Xellia Pharmaceuticals APS (DK)

( * ) Notice: Subject to any disclaimer, the term of this patent is extended or adjusted under 35 U.S.C. 154(b) by 0 days.

(21) Appl. No.: 13/389,597

(22) PCT Filed: Aug. 11, 2010

(86) PCT No.: PCT/NO2010/000301
§ 371 (c)(1),
(2), (4) Date: Feb. 9, 2012

(87) PCT Pub. No.: WO2011/019285
PCT Pub. Date: Feb. 17, 2011

(65) Prior Publication Data
US 2012/0142893 A1 Jun. 7, 2012

Related U.S. Application Data

(60) Provisional application No. 61/233,838, filed on Aug. 14, 2009.

(51) Int. Cl.
B01D 11/00 (2006.01)
B01D 12/00 (2006.01)
B01D 17/00 (2006.01)
C02F 1/26 (2006.01)
C02F 1/28 (2006.01)
B01D 15/08 (2006.01)
C07K 1/20 (2006.01)
C07K 7/64 (2006.01)

(52) U.S. Cl.
CPC .... C07K 1/20 (2013.01); C07K 7/64 (2013.01)
USPC ............ 210/511; 210/634; 210/635; 210/656

(58) Field of Classification Search
CPC .................. C07K 1/20; C07K 6/64
See application file for complete search history.

(56) References Cited

U.S. PATENT DOCUMENTS

| 5,021,341 A | 6/1991 | Giacobbe et al. | |
| 2007/0010655 A1* | 1/2007 | Antia et al. | 530/315 |
| 2008/0293959 A1* | 11/2008 | Liu et al. | 556/449 |

FOREIGN PATENT DOCUMENTS

WO 2005026323 A2 3/2005

OTHER PUBLICATIONS

Schwartz et al, Pneumocandins from Zalerion arboricola 1. Discovery and Isolation, Journal Antibiot, Dec. 1992;45(12):1853-66.*
Zhuravlev et al, The surface chemistry of amorphous silica. Zhuravlev model, Colloids and Surfaces A: Physicochemical and Engineering Aspects 173 (2000) 1-38.*
Stulik et al, Stationary phases for peptide analysis by high performance liquid chromatography: a review, Analytica Chimica Acta 352 (1997) 1-19.*
Advanced Materials Technology (Halo column. [online]. Advanced materials biotechnology, 2006 [retrieved on Jun. 24, 2013]. Retrieved from the Internet: <URL: http://www.advanced-materials-tech.com/halo.html >).*
Sigma-Aldrich, (Ascentis Express HPLC Columns with Fused-Core Technology. [online]. Sigma-Aldrich, 2008 [retrieved on Jun. 24, 2013]. Retrieved from the Internet: <URL: http://www.lsc.gr/attachments/File/ASCENTIS_EXPRESS.pdf>).*
Osawa AE et al, "Purification of pneumocandins by preparative silica gel high performance liquid chromatography", Journal of Chromotography, vol. 831, No. 2, (Jan. 29, 1999), pp. 217-225.
Roush et al, "Preparative high-performance liquid chromatography of echinocandins", Journal of Chromatography, vol. 827, No. 2 (Dec. 11, 1998) pp. 373-389.
Risley et al, "Chiral separations of polar compounds by hydrophilic interaction chromatography with evaporative light scattering detection", Analytical Chemistry, vol. 72, No. 8 (Apr. 15, 2000) pp. 1736-1739.
Lin Xucong et al, "Glycin.bonded silica monolithic column as zwitterionic stationary phase for hydrophilic interaction pressurized capillary electrochromatography", Journal of Separation Science, vol. 32, No. 15-16 (Jul. 13, 2009) pp. 2767-2775.
Naidong Weng, "Bioanalytical liquid chromatography tandem mass spectrometry methods on underivatized silica columns with aqueous/organic mobile phase", Analytical Journal of Chromatography. B: Analytical Technologies in the Biomedical and Life Sciences, vol. 796, No. 2 (Nov. 5, 2003) pp. 209-224.
Zhuravlev et al.; "The Surface Chemistry of Amorphous Silica. Zhuravlev Model"; Physicochemical and Engineering Aspects; 173; pp. 1-38; (2000).
Adefarati et al.; "Pneumocandins from Zalerion Arboricola V. Glutamic Acid-and Leucine-Derived Amino Acids in PneumocandinA0 (L-671,329) and Distinct Origins of the Substituted Proline Resides in Pneumocandins A0 and B0"; The Journal of antibiotics; 45(12); pp. 1953-1957; (1992).
Hensens et al.; "Pneumocandins From Zalerion Arboricola III. Structure Elucidation"; The Journal of Antibiotics; 45 (12); pp. 1875-1885; (1992).
Hoffman et al.; "Transition Metal-Mediated Separation of Isomeric Pneumocandins by Capillary Electrochromatography"; J. High Resol. Chromatogr.; 22(6); pp. 309-314; (1999).
Hsieh, Yunsheng; "Potential of HILIC-MS in Quantitative Bioanalysis of Drugs and Drug Metabolites"; J. Sep. Sci.; 31; pp. 1481-1492; (2008).
Masurekar et al.; "Pneumocandins From Zalerion Arboricola, II. Modification of Product Spectrum by Mutation and Medium Manipulation"; The Journal of Antibiotics; 45(12); pp. 1867-1874; (1992).

(Continued)

Primary Examiner — Marcela M Cordero Garcia
Assistant Examiner — Sergio Coffa
(74) Attorney, Agent, or Firm — Cantor Colburn LLP

(57) ABSTRACT

The present invention concerns a method for separation of the antifungal cyclic hexapeptides Pneumocandin $B_0$ from Pneumocandin $C_0$ using a hydrophilic stationary phase and a hydrophobic mobile phase.

15 Claims, 2 Drawing Sheets

(56) References Cited

OTHER PUBLICATIONS

Nti-Gyabaah et al.; "Normal Phase High-Performance Liquid Chromatography of Pneumocandins: In Situ Modifiction of Silica with L-Proline to Separate Structural Analogues"; Biotechnol. Prog. 22; pp. 538-546; (2006).

Schmatz et al.; "Pneumocandins From Zalerion Arboricola IV. Biological Evaluation of Natural and Semisynthetic Pneumocandins for Activity Against *Pneumocystis* Carinii and Candida Species"; The Journal of Antibiotics; 45(12); pp. 1886-1891; (1992).

Schwartz et al.; "Pneumocandins From Zalerion Arboricola"; The Journal of Antibiotics; 45(12); pp. 1853-1866; (1992).

Shou et al.; "Ultrafast Liquid Chromatography/Tandem Mass Spectrometry Bioanalysis of Polar Analytes Using Packed Silica Columns"; Rapid Communications in Mass Spectrometry; 16; pp. 1613-1621; (2002).

International Search Report and Written Opinion; International Application No. PCT/NO2010/000301; International Filing Date Aug. 11, 2010; Date of Mailing Oct. 13, 2010; 15 pages.

Lerro et al.; "Separation of the Sticky Peptides from Membrane Proteins by High-Performance Liquid Chromatography in a Normal-Phase System"; Analytical Biochemistry; 215; 38-44; (1993).

Ascentis Express HPLC Columns with Fused-Core Technology, Extreme Performance on Any LC System, SUPELCO Analytical; Sigma-Aldrich.com/express; http://www.lsc.gr/attachments/File/ASCENTIS EXPRESS.pdf; 16 pages; printed Jun. 20, 2013.

\* cited by examiner

SEPARATION AND/OR PURIFICATION OF $B_0$ FROM $C_0$

FIELD OF THE INVENTION

The present invention concerns methods for separating and purifying Pneumocandin compounds.

BACKGROUND

Pneumocandins are antifungal cyclic hexapeptides with a lipid side chain (see Schwarts et al, 1992, Journal of antibiotics, Vol 45, No 12, pages 1853-1866, Masurekar et al, 1992, Journal of Antibiotics, Vol 45, No. 12, pages 1867-1874, Hensens et al, 1992, Journal of Antibiotics, Vol 45, No 12, pages 1875-1885, Schmatz et al, 1992, Journal of Antibiotics, Vol 45, No 12, pages 1886-1891 and Adefarati et al, 1992, Journal of Antibiotics, Vol 45, No 12, pages 1953-1957 and U.S. Pat. No. 5,021,341)

The antifungal activity of Pneumocandins is connected to inhibition of the biosynthesis of 1,3β-glucans. 1,3β-glucan synthase, a multisubunit enzyme, is responsible for fungal cell wall construction, division septum deposition, and ascospore wall assembly. The catalytic subunit of this enzyme complex, an integral membrane protein, has been identified both in model yeasts *Saccharomyces cerevisiae* and *Schizosaccharomyces pombe*, and in pathogenic fungi such as *Candida, Aspergillus, Cryptococcus* and *Pneumocystis* species". (Curr Drug Targets Infect Disord. 2001 August; 1(2): 159-69 by Liu and Balasubramanian).

The Pneumocandins and Pneumocandin derivatives are useful as active pharmaceutical ingredients (APIs) and/or intermediates for producing APIs. Drugs comprising the APIs are intended for use in therapeutic or prophylactic treatment of diseases or conditions involving fungal infections.

For example, the API Caspofungin is a semi synthetic derivative of Pneumocandin $B_0$. Caspofungin, marketed as Cancidas®, is indicated in adults and pediatric patients (3 months and older) for:

Empirical therapy for presumed fungal infections in febrile, neutropenic patients.

Treatment of Candidemia and the following *Candida* infections: intra-abdominal abscesses, peritonitis and pleural space infections.

Treatment of Esophageal Candidiasis.

Treatment of Invasive Aspergillosis in patients who are refractory to or intolerant of other therapies Thus, high purity of the API is required for safety and efficacy of the drugs. Pneumocandin $B_0$ can be used as a starting material for producing Caspofungin. During such production, Pneumocandin $C_0$ will be regarded as an impurity. Thus it is desirable to separate Pneumocandin $B_0$ from Pneumocandin $C_0$, or even purify Pneumocandin $B_0$ from Pneumocandin $C_0$.

Pneumocandin $B_0$ is often produced by fermentation of the fungus *Glarea lozoyensis* (earlier classified as *Zalerion arboricola*), but many isomers and derivatives with similar physiochemical properties, are coproduced in the fermentation processes.

Pneumocandin $B_0$ and Pneumocandin $C_0$ are isomers which differ by the position of one hydroxyl group at a proline residue only:

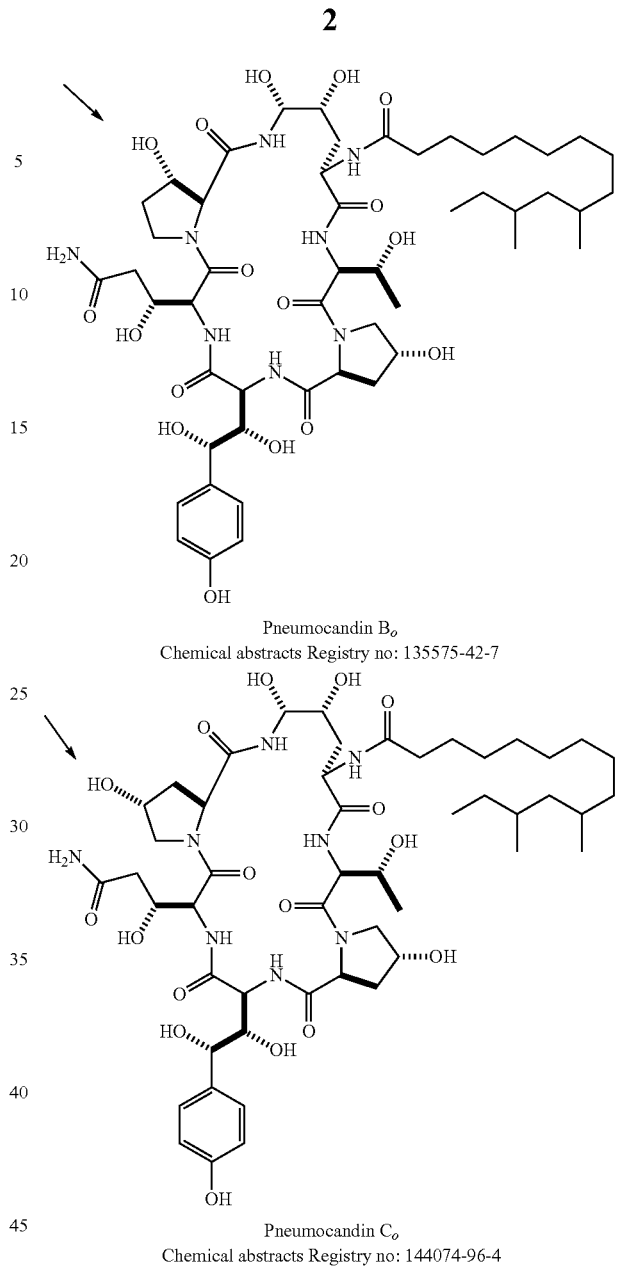

Pneumocandin $B_o$
Chemical abstracts Registry no: 135575-42-7

Pneumocandin $C_o$
Chemical abstracts Registry no: 144074-96-4

Several methods for separation of Pneumocandin $B_0$ from the other Pneumocandins (e.g Pneumocandin $A_0$, $B_5$, $D_0$, $E_0$) are known. However, crystallization and reverse phase chromatography methods have been unable to separate Pneumocandin $B_0$ from Pneumocandin $C_0$. These two isomers differ only by the position of one hydroxyl group at a proline residue.

For the separation of Pneumocandin $B_0$ from Pneumocandin $C_0$, normal phase chromatography utilizing ethyl acetate/methanol/water mobile phases has been used. This method, however, suffers from low Pneumocandin solubility in the loading solution and also from somewhat low robustness. In addition, this mobile phase is not very compatible with mass spectrometric methods, which limits the usefulness of the method for analytical purposes.

SUMMARY OF THE INVENTION

This invention provides for separation and purification of Pneumocandin compounds.

More specifically it provides a method for purification of Pneumocandin $B_0$.

Even more specifically, it provides a method for purification of $B_0$ using a hydrophilic stationary phase and hydrophobic mobile phase.

In one embodiment, the hydrophilic stationary phase comprises silica.

In another embodiment, the mobile phase comprises acetonitrile, water and ammonium acetate.

In another embodiment, this invention provides a method for separation of Pneumocandin $B_0$ from other compounds.

In another embodiment, this invention provides a method for separation of Pneumocandin $B_0$ from other Pneumocandins.

In yet another embodiment, this invention provides a method for separation of Pneumocandin $B_0$ from Pneumocandin $C_0$.

This method provides very fast separation of $B_0$ from $C_0$ using a mobile phase which is compatible with mass spectrometric methods.

DETAILED DESCRIPTION

Definitions

Figure 1:
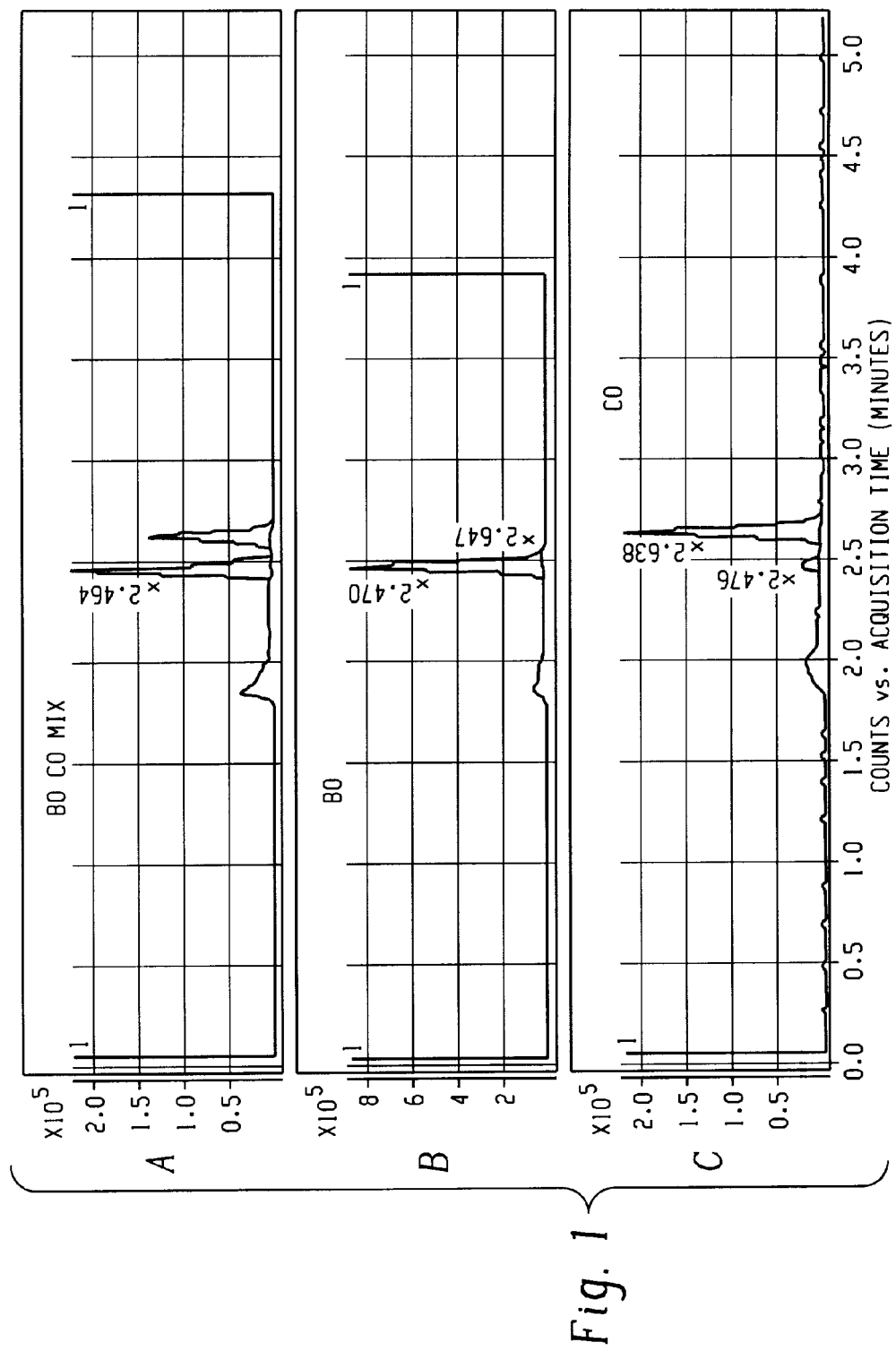
FIG. 1. shows selective mass chromatograms from different LC-MS experiments. (A) Chromatographic separation of Pneumocandin $B_0$ from Pneumocandin $C_0$ in a mixture containing both isomers. (B) Identification of the Pneumocandin $B_0$ peak using a pure Pneumocandin $B_0$ reference standard. (C) Identification of the Pneumocandin $C_0$ peak using a pure Pneumocandin $C_0$ reference standard.

As used herein, the following terms and expressions are meant to have the meanings defined below.

"Pneumocandins" are cyclic hexapeptides or derivatives thereof comprising a lipid moiety with antifungal activity.

"Pneumocandin $B_0$" is a compound with the following structure:

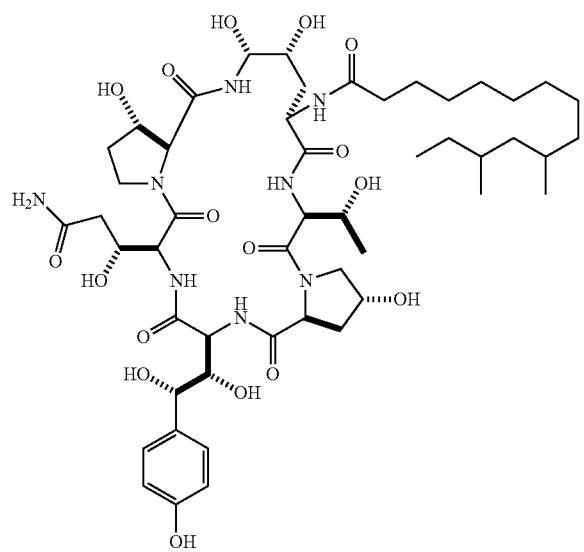

However, the term "Pneumocandin $B_0$", as used herein, also includes salts or stereo isomers thereof.

"Pneumocandin $C_0$" is a compound with the following structure

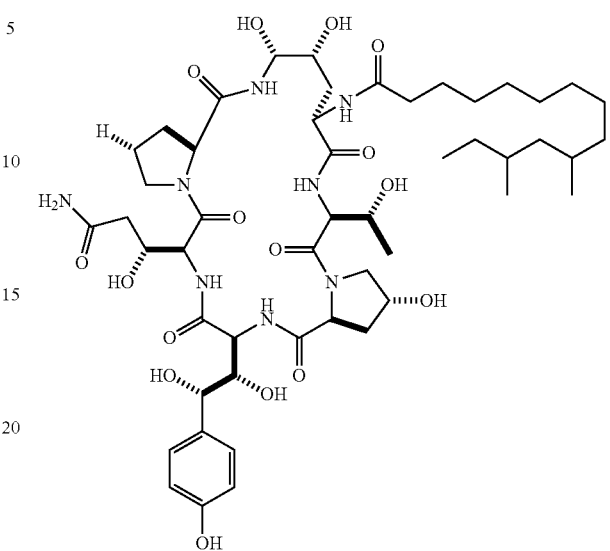

However, the term "Pneumocandin $C_0$", as used herein, also includes salts or stereo isomers thereof.

"Separation" is any method wherein a desired compound is resolved from another (analytically or preparatively).

"Purification" is any separation method by which the concentration of a desired compound is increased.

"Chromatography" is any purification technique involving a stationary phase and a mobile phase.

"A stationary phase" is any surface comprising ligands capable of retaining compounds.

"Ligands" are moieties of the stationary phase, at which the binding of compounds occurs.

"A mobile phase" is any fluid, solvent, liquid or mixture that can percolate through or along the stationary phase in a definite direction.

"A hydrophobic mobile phase" is any mobile phase comprising a high percentage of an organic solvent and a low percentage of an aqueous solution (e.g formic acid or TFA) and/or a buffer (e.g ammonium acetate or ammonium formate).

"Reverse phase chromatography" is any chromatography in which the more polar or charged components are eluted before the less polar ones.

"Normal phase chromatography" is any chromatography in which the more polar or charged components are eluted later than the less polar ones.

"High percentage" means between 60%-100%

"Low percentage" means between 0%-40%

"% v/v" means volume percentage

HILIC is any chromatographic technique employing a hydrophilic stationary phase and aqueous-organic solvent mobile phases.

The present invention allows separation and purification of Pneumocandin compounds by chromatography, especially hydrophilic interaction chromatography (HILIC), also known as hydrophilic interaction liquid chromatography.

Without being bound by theory, it is believed that during HILIC purification a liquid-liquid extraction system is created. The mobile phase forms a water-rich layer on the surface of the highly polar stationary phase. The analytes are distributed between the water-rich stationary layer with high-aqueous contents and the mobile phase with mostly organic contents. The analytes possessing higher polarity will have a higher affinity to the stationary aqueous layer than the analytes possessing weaker polarity. Thus, a separation based on a compound's polarity and degree of solvation probably takes place. However, the exact mechanism of HILIC is still unresolved in the field.

There are several types of polar stationary phases, such as e.g. unmodified silica, amino, and zwitterionic (ZIC) columns commercially available for HILIC separation/purification.

For the present invention, unmodified silica surfaces comprising silanols and/or siloxanes are preferred.

HILIC often provides a high-organic and low-aqueous mobile phase which is MS favourable in terms of sensitivity.

It is preferred that the mobile phase contains a high percentage of an organic solvent (e.g ACN) and a low percentage of an acidic aqueous solution (e.g formic acid or TFA) and/or a buffer (e.g ammonium acetate or ammonium formate).

The Pneumocandin sample is dissolved into the mobile phase and passed through the stationary phase and is thereby allowed to be separated. In this way, Pneumocandin $B_0$ may be separated from Pneumocandin $C_0$ or from other Pneumocandins. This chromatographic separation may be performed either in preparative or analytical scale.

This invention provides a method for separation and purification of Pneumocandin compounds.

More specifically it provides a method for purification of Pneumocandin $B_0$.

Even more specifically, it provides a method for purification of $B_0$ using a hydrophilic stationary phase and hydrophobic mobile phase.

The hydrophobic mobile phase could comprise 60%-98% acetonitrile, or more preferred 75%-95% acetonitrile or even more preferred 80%-90% acetonitrile or most preferred 85%-87% acetonitrile.

The hydrophobic mobile phase could comprise 2%-40% of aqueous solutions, or more preferred 5%-25% of aqueous solutions or even more preferred 10%-20% aqueous solutions or most preferred 13%-15% aqueous solutions.

In one embodiment, the hydrophilic stationary phase comprises silica.

In another embodiment, the mobile phase comprises acetonitrile, water and ammonium acetate.

In another embodiment, this invention provides a method for separation of Pneumocandin $B_0$ from other compounds.

In another embodiment, this invention provides a method for separation of Pneumocandin $B_0$ from other Pneumocandins.

In yet another embodiment, this invention provides a method for separation of Pneumocandin $B_0$ from Pneumocandin $C_0$.

To be able to create an analytical method to analyze the content of $B_0$ and $C_0$ in a sample it was necessary to either separate the two compounds chromatographically or find compound specific ions, qualifiers or MS/MS-transitions. Since either of the $B_0$ or $C_0$ standards supplied were pure enough, we had to develop a fast separation of $B_0$ or $C_0$ before further MS-experiments could be done. Since reverse phase chromatography did not show any promising results, it was decided to try and set up a method based on normal phase chromatography. Initial testing was done on an Agilent-NH$_2$ column, with different combinations of Acetonitrile (ACN) and 0, 1% Ammonium Acetate solution in water (AmAc) which showed signs of separation, but the resolution was far from good enough to give a base line separation of the two compounds. An Ascentis Express HILIC column, from Sigma-Aldrich was then tested based on that it is a "normal phase" type of column and that the Fused-Core particle technology is known to give good resolution. After testing out different combinations of ACN and AmAc a mixture of 85/15 (ACN/AmAc) was chosen. The result was a baseline separation of $B_0$ and $C_0$. Increasing the ACN content gave longer retention times but broader peaks, and increasing the AmAc content gave shorter retention times but less separation. $B_0$ and $C_0$ were monitored with ESI/MS in positive mode.

This method provides surprisingly fast separation of $B_0$ from $C_0$ with a mobile phase that is compatible with mass spectrometric methods (the mobile phase being volatile and gives high ionization efficiency). The method can separate $B_0$ from $C_0$ in less than 5 minutes or even less than 3 minutes.

The following abbreviations are used with the specified meanings throughout this specification:

ABBREVIATIONS

API—Active Pharmaceutical Ingredients
HILIC—Hydrophilic Interaction Liquid Chromatography
LC—Liquid Chromatography
HPLC—High Performance Liquid Chromatography
MS—Mass Spectrometry
MS/MS—Tandem Mass Spectrometry
ESI/MS—Electrospray Ionization Mass Spectrometry
TOF—Time of Flight
ZIC—Zwitterionic Column
ACN—Acetonitrile
AmAc—Ammonium Acetate
TFA—Trifluoracetic Acid

EXAMPLES

Example I

In this experiment, an Agilent 1200 HPLC system coupled to an Agilent 6520 Q-TOF mass spectrometer was used. The Agilent 1200 HPLC system consisted of a binary pump, degasser, thermostated autosampler and a thermostated column compartment (set to 25° C.). A Supelco Ascentis Express HILIC 15 cm×4.6 mm, 2.7 µm column was used. The mobile phase consisted of 15% v/v 0.1% w/w ammonium acetate pH 4.5 and 85% v/v ACN. The flow rate was 1 ml/min. FIG. 1A shows that this chromatographic set-up is able to separate Pneumocandin $B_0$ from Pneumocandin $C_0$ in a mixture containing both isomers. FIG. 1B shows the identification of the Pneumocandin $B_0$ peak using a pure Pneumocandin $B_0$ reference standard. FIG. 1C shows the identification of the Pneumocandin $C_0$ peak using a pure Pneumocandin $C_0$ reference standard.

The chromatographic separation and retention times could be affected by altering the ACN or ammonium acetate contents. Increasing the ACN content resulted in longer retention times and broader peaks. Increasing the ammonium acetate content resulted in shorter retention times and decreased separation.

Example II

Figure 2:
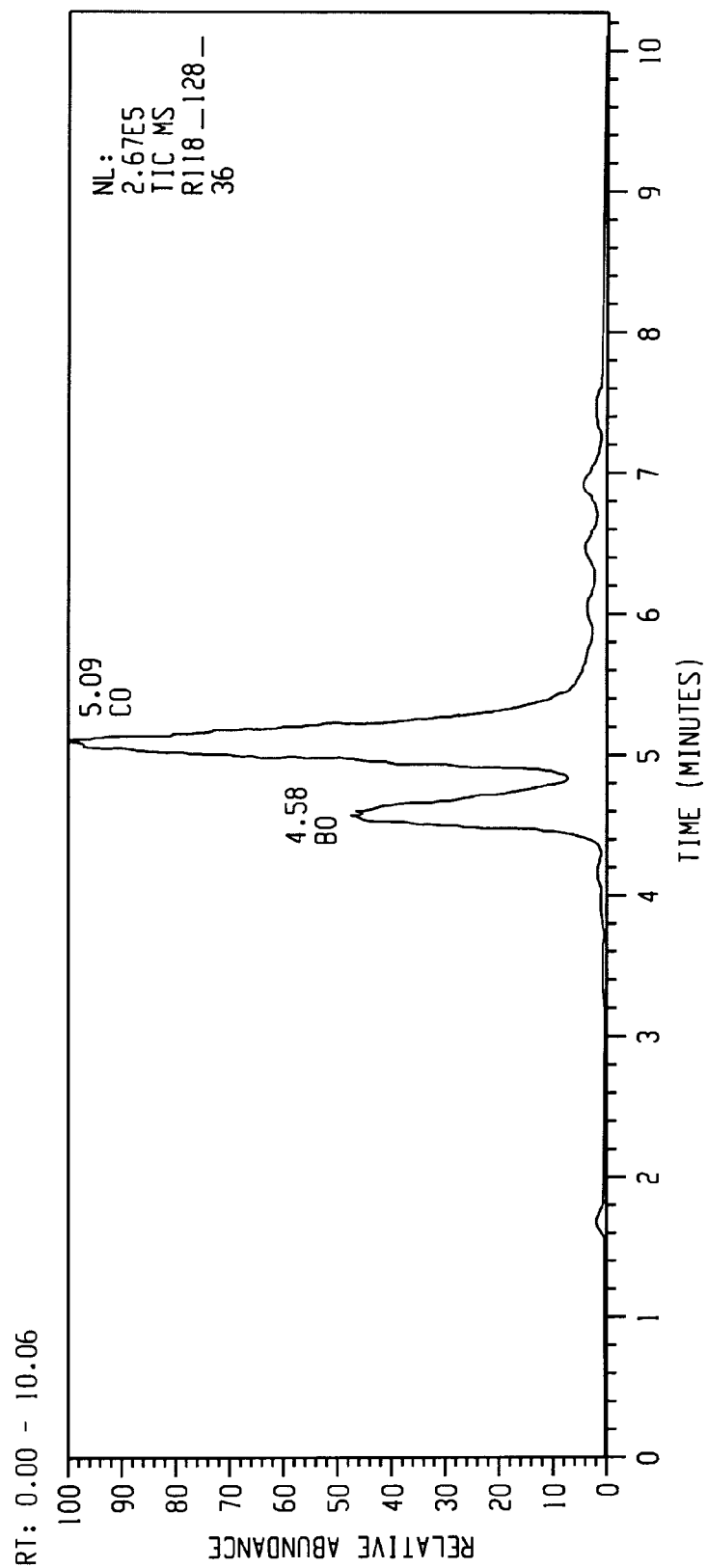
FIG. 2 shows that the chromatographic set-up of Example 2 is able to separate Pneumocandin $B_0$ from Pneumocandin $C_0$ in a sample containing both isomers.

In this experiment, a Thermo Fisher Surveyor HPLC system was used. The Surveyor HPLC system consisted of a quaternary pump, degasser, thermostated autosampler and a thermostated column compartment (set to 40° C.). A Supelco Ascentis Si HILIC 15 cm×2.1 mm, 5 µm column was used. The mobile phase consisted of 13% v/v 0.1% w/w ammonium acetate pH 4.5 and 87% v/v ACN. The flow rate was 0.2 ml/min. FIG. 2 shows that this chromatographic set-up is able to separate Pneumocandin $B_0$ from Pneumocandin $C_0$ in a sample containing both isomers

PRIOR ART

Several publications describe methods for purification of Pneumocandins.

Purification of Pneumocandins by preparative silica-gel high-performance liquid chromatography Journal of Chromatography A, 831 (1999) 217-225 by Osawaa et al.

Preparative high-performance liquid chromatography of echinocandins Journal of Chromatography A, Volume 827, Issue 2, 11 Dec. 1998, Pages 373-389 by Roush et al.

Normal Phase High-Performance Liquid Chromatography of Pneumocandins: In Situ Modification of Silica with L-Proline To Separate Structural Analogues Biotechnol Prog. 2006 March-April; 22(2):538-46 by Nti-Gyabaah et al.

Ultrafast liquid chromatography/tandem mass spectrometry bio analysis of polar analytes using packed silica columns Rapid Commun Mass Spectrom. 2002; 16(17):1613-21 by Shou et al WO2005026323 STATIONARY PHASES AND A PURIFICATION PROCESS USING THE STATIONARY PHASES Transition Metal-Mediated Separation of Isomeric Pneumocandins by Capillary Electrochromatography J. High Resol. Chromatogr., 1999, 22(6): 309-314 by Hoffman and Dovletoglou Potential of HILIC-MS in quantitative bio analysis of drugs and drug metabolites J. Sep. Sci. 2008, 31, 1481-1491 by Hsieh

The invention claimed is:

1. A method for separation of Pneumocandin $B_0$ from Pneumocandin $C_0$ comprising providing a HILIC chromatographic separation apparatus comprising a hydrophilic stationary phase and a hydrophobic mobile phase, wherein the hydrophobic mobile phase comprises 80%-90% v/v acetonitrile and 10%-20% v/v of an acidic aqueous solution, dissolving a sample containing Pneumocandin $B_0$ together with Pneumocandin $C_0$ into the hydrophobic mobile phase, passing the mobile phase through the stationary phase, wherein Pneumocandin $B_0$ is allowed to separate from Pneumocandin $C_0$ or any other Pneumocandin present in the sample.

2. The method of claim 1, wherein the separation is a purification.

3. The method of claim 1, wherein the stationary phase comprises silica.

4. The method of claim 1, wherein the stationary phase comprises siloxane groups.

5. The method of claim 1, wherein the stationary phase comprises silanol groups.

6. The method of claim 1, wherein the stationary phase comprises siloxane and silanol groups.

7. The method of claim 1, wherein the stationary phase is neutral.

8. The method of claim 1, wherein the acidic aqueous solution is an ammonium acetate solution.

9. The method of claim 1, wherein the mobile phase further comprises ammonium acetate.

10. The method of claim 1, wherein the mobile phase comprises 15% v/v of 0.1% w/w aqueous ammonium acetate and 85% v/v acetonitrile.

11. The method of claim 1, wherein separation time is less than 5 minutes.

12. The method of claim 1, wherein separation time is less than 3 minutes.

13. The method of claim 1, wherein the stationary phase comprises silica and is neutral.

14. The method of claim 1, wherein the hydrophilic stationary phase comprises fused core particles surrounded by a porous shell.

15. The method of claim 14, wherein the porous shell is silica.

* * * * *